United States Patent [19]
Chilcott et al.

[11] Patent Number: 5,645,831
[45] Date of Patent: Jul. 8, 1997

[54] BACILLUS THURINGIENSIS STRAIN AND METABOLITE WHICH ARE ACTIVE AGAINST CORN ROOTWORM

[75] Inventors: Chris N. Chilcott; Peter Wigley; Andrew Broadwell, all of Auckland, New Zealand; Sherry Darlene Heins; Pamela Gail Marrone, both of Davis, Calif.

[73] Assignees: BioDiscovery New Zealand Ltd., Auckland, New Zealand; AgraQuest, Inc., Davis, Calif.

[21] Appl. No.: 621,774

[22] Filed: Mar. 22, 1996

[51] Int. Cl.$^6$ .................................................. A01N 63/02
[52] U.S. Cl. ................ 424/93.461; 424/405; 435/252.31
[58] Field of Search ............................. 424/93.461, 405; 435/41, 252.31, 832

[56] References Cited

U.S. PATENT DOCUMENTS

| | | | |
|---|---|---|---|
| 4,190,495 | 2/1980 | Curtiss, III | 435/172.3 |
| 4,968,619 | 11/1990 | Curtiss, III | 435/252.33 |
| 4,999,192 | 3/1991 | Payne et al. | 424/93.461 |
| 5,208,017 | 5/1993 | Bradfisch et al. | 424/84 |
| 5,427,786 | 6/1995 | Payne et al. | 424/93.461 |

FOREIGN PATENT DOCUMENTS

WO95/25181  9/1995  WIPO.

OTHER PUBLICATIONS

Stonard et al., "Microbial secondary metabolites as a source of agrochemicals" *ACS Symposium Series* (1994) 551:25.
Birge, *Bacterial and Bacteriophage Genetics* (1981). A title page and table of contents is included herewith.
Spear, "Genetic engineering of bacterial insecticides" *Biotechnology in Agricultural Chemistry* (1987) pp. 204–214.
Johnson et al., (1993) "Insecticidal Activity of EG4961, a Novel Strain of *Bacillus thuringiensis* Toxic to Larvae and Adults of Southern Corn Rootworm (Coleoptera: Chrysomelidae) and Colorado Potato Beetle (Coleoptera: Chrysomelidae)," *J. Economic Entomol.* 86(2):330–333.
Chilcott et al (1993) J. Invert. Pathol. 61:244–247 "Isolation and toxicity of *Bacillus thuringiensis* from soil and insect habitats in New Nealand".

*Primary Examiner*—Robert A. Wax
*Assistant Examiner*—Daniel Mytelka
*Attorney, Agent, or Firm*—Morrison & Foerster

[57] ABSTRACT

The present invention relates to a newly isolated *Bacillus thuringiensis* strain which exhibits insecticidal activity. The supernatant of cultures of this novel strain is also an effective insecticidal agents. Also included in the invention are the novel *B. thuringiensis* isolate, its supernatant and a solvent extract of the supernatant which are specifically active against corn rootworm but not against beet armyworm, nematodes or flies. These strains and supernatants may be used to treat plants infected with susceptible organisms.

7 Claims, No Drawings

BACILLUS THURINGIENSIS STRAIN AND METABOLITE WHICH ARE ACTIVE AGAINST CORN ROOTWORM

CROSS-REFERENCE TO RELATED APPLICATIONS

An application regarding strains 189/194/196 (file reference: 31141-20003.00) to nematicidal *B. thuringiensis* strains and supernatants.

FIELD OF THE INVENTION

This invention is in the field of biopesticides. More particularly, the present invention describes a novel, insecticidal strain of the bacterium *Bacillus thuringiensis* which is selectively active against corn rootworm (e.g., *Diabrotica virgifera, D. longicornis* and *D. undecimpunctata*). This novel *B. thuringiensis* strains produces a secondary metabolite in its supernatant which can be used as a biocontrol agent in the treatment and prevention of corn rootworm infection in plants.

BACKGROUND OF THE INVENTION

Every year 250 to 350 million dollars of chemical pesticides are used to control corn rootworm infections. Synthetic chemical pesticides are relatively expensive and, because of their toxicity to humans and wildlife, many have been banned from use. Many of the chemicals used for corn rootworm control are toxic to humans, wildlife and other nontarget species. Also, some have leaked into the ground water. As a result, much research has been concentrated in the area of biopesticides which have the advantage of being cheaper to produce and safer for the environment.

One commonly used biopesticide is the gram-positive bacterium *Bacillus thuringiensis*. Pesticidal *B. thuringiensis* strains are known to produce crystal proteins during sporulation which are specifically toxic to certain orders and species of insects and nematodes. (See, e.g., U.S. Pat. No. 4,999,192 and U.S. Pat. No. 5,208,017). Proteinaceous endotoxins produced by *B. thuringiensis* also act as insecticidal agents against corn rootworm and other beetles. For instance, delta-endotoxin is synthesized by the *B. thuringiensis* sporulation cell and, upon ingestion by susceptible larvae, is transformed into a biologically-active moiety that destroys the gut epithelium of the insect. (See, e.g., U.S. Pat. No. 5,427,786 to Payne et al.). Although *B. thuringiensis* endotoxins have been shown to be effective pesticides as purified crystals, washed cell pellets and expressed proteins, none of their supernatants have exhibited pesticidal activity.

Other *B. thuringiensis* thermostable proteins, termed beta-exotoxins, have also been shown to have pesticidal properties. Burgjeron and Biache (1979), *Entomophaga:* 11:279-284 report beta-exotoxins that are active against the Colorado potato beetle (*Leptinotarsa decemlineata*). In addition, known *B. thuringiensis* beta-exotoxins exhibit non-specific pesticidal activity; killing not only nematodes, but flies, armyworms and corn rootworms as well.

Stonard et al. (1994) ACS Symposium Series 551:25 report a water soluble secondary metabolite active against corn rootworm in the supernatant of a *Bacillus cereus* strain. Thus, there is a need for pesticidal *B. thuringiensis* strains which produce non-exotoxin active metabolites in their supernatant. There is also a need for a biocontrol agents which are specifically active against corn rootworm.

SUMMARY OF THE INVENTION

An isolated, pure culture of a novel *Bacillus thuringiensis* strain BD#32 or mutants thereof exhibiting insecticidal activity is provided. Also provided is an insecticidal supernatant and an insecticidal solvent-extract of the supernatant obtained from culturing this novel strain. In addition, an isolated, pure culture and its supernatant specifically active against corn rootworm is provided.

DESCRIPTION OF THE PREFERRED EMBODIMENTS

The present invention provides a novel isolate of a *Bacillus thuringiensis* strain which exhibits pesticidal activity. This strain is designated BD#32 and was isolated from mud taken from Opito Bay, Coro Mandel Peninsula, New Zealand. This strain was deposited with the NRRL on Mar. 13, 1996 the provisions of the Budapest Treaty on the International Recognition of the Deposit of Microorganisms for the Purposes of Patent Procedure under Accession No. B-21530. Another aspect of the invention is the pesticidal activity of the culture broth in which this novel strain is grown. The claimed isolate produces a non-exotoxin, solvent-extractable, non-proteinaceous metabolite that is 100% effective in killing corn rootworm. The biopesticide produced by the bacterial strain of the subject invention is unique because it is active against corn rootworm but inactive against flies. This novel strain has many advantages over chemical pesticides, particularly with respect to cost and environmental safety.

As used herein, the term "insects" includes all organisms included in the class "Insecta." "Pre-adult" insects refers to any form of an organism prior to the adult stage, including, for example, eggs, larvae and nymphs. "Insecticidal" refers to the ability of a substance to increase mortality or inhibit the growth rate of insects. "Nematicidal" means the ability of a substance to increase mortality or inhibit the growth rate of nematodes. "Pesticidal" refers to the ability of a substance to increase mortality or inhibit the growth rate of insects, nematodes and flies. "Stunting" refers to a decreased rate of growth or abnormal development.

"Supernatant" refers to the liquid broth remaining when the cells grown in the broth are removed by centrifugation, filtration, sedimentation or any other means known in the art. The term "culturing" refers to the propagation of organisms on or in media of various kinds. The term "positive control" means a compound known to have pesticidal activity. "Positive controls" include, but are not limited to, commercially-available chemical pesticides. The term "negative control" means a compound known not to have pesticidal activity. Examples of negative controls include water or ethyl acetate.

The term "solvent" includes any liquid that holds another substance in solution. "Solvent extractable" refers to any compound which dissolves in a solvent and which then may be isolated from the solvent. Examples of solvents, include, but are not limited to, organic solvents like ethyl acetate.

As used herein, an "agent" includes natural or synthetic products, microorganisms, plant extracts and chemicals. A "test compound" is the agent being assayed for nematicidal or insecticidal properties.

The *B. thuringiensis* strain of this invention may be grown in any conventional growth medium that supports *Bacillus spp.* Examples of suitable broth for culturing *B. thuringiensis*, include but are not limited to, a broth composed of peptone, dextrose, yeast extract and malt extract and a broth using the same ingredients as well as proflo cottonseed extract and soy flour. Solid substrates are also suitable for growing *B. thuringiensis* strains. Growth procedures may also be readily scaled up to large fermentors by methods well known in the art.

Unlike known insecticidal *B. thuringiensis* isolates, the novel strain of this invention produces an insecticidal agent which is found in the supernatant when this strain is grown in culture. The supernatant may be obtained by any conventional means including centrifugation, filtration, sedimentation or the like.

Solvent extracts may be obtained by any means known in the art. For example, aqueous supernatant may be mixed with an organic solvent and the two phases separated. The solvent phase may then be evaporated to obtain a dried organic extract. Other methods of obtaining solvent extracts will be known to those of ordinary skill in the art.

Another aspect of the invention provides mutants or derivatives of the BD#32 strain which retain insecticidal activity and produce insecticidal agents in their supernatant. Such mutants or derivatives have altered genotypic or phenotypic characteristics, and may be produced by genetic manipulation techniques known in the art. (See, e.g., U.S. Pat. No. 4,190,495; U.S. Pat. No. 4,968,619; Edward A. Birge, BACTERIAL AND BACTERIOPHAGE GENETICS, (1981) and Brian B. Spear, BIOTECHNOLOGY IN AGRICULTURAL CHEMISTRY, 204–214 (1987)) Examples of genetic mutants include, but are not limited to, mutants selected for phenotype by classical genetic methods and mutants created using recombinant techniques.

All patents and publications cited herein are incorporated by reference.

The following examples are provided to illustrate the invention. These examples are not to be construed as limiting.

EXAMPLE 1

Culturing of novel *Bacillus thuringiensis* strain

Bacillus samples were grown in two commonly used Bacillus culture media. Medium 1 contained peptone, dextrose, yeast extract and malt extract. Medium 2 contained the same ingredients and, in addition, proflo cottonseed extract and soy flour. One day old streaked cultures were used to inoculate either 250 mL baffled shake flasks or 15 mL culture tubes. Flasks or tubes were shaken at 200 rpm at 29° C. for 5 days. To assay insecticidal activity, 35 mls of culture broth were centrifuged at 5,200 rpm for 20 minutes and the supernatant used in microassay described in Example 2.

EXAMPLE 2

Assaying insecticidal activity of Bacillus strain

Assays were performed in 96-well microplates. Each well contained a solid agar substrate, a test organism suspension and either a positive control, a negative control or supernatant obtained as described in Example 1 from the Bacillus strain.

Test organisms used were either pre-adult corn rootworms, pre-adult beet armyworms (*Spodoptera exigua*), pre-adult flies (*Drosophila melanogaster*) or the N2 strain of the nematode *Caenorhabditis elegans*. Test organisms were diluted in 0.1% agar to a concentration of approximately 5 organisms/25 ul.

To assay pesticidal activity, an agar substrate was prepared for the wells of the microplate by pouring 975 mls of deionized water into a 1 liter bottle. Three grams of sodium chloride (NaCl), 2.5 grams of peptone, 17.0 grams of bactoagar and 1.0 mL of a 5 mg/ml solution of cholesterol in ethanol were added to the bottle. The contents were sterilized at a minimum of 15 psi, 250° F. for 30 minutes. After sterilization, 1.0 ml of a filter-sterilized 1M $CaCl_2$ solution, 1.0 ml of a filter sterilized 1M $MgSO_4$ solution, and 25.0 ml of a filter sterilized, 1 M, pH 6.0 solution of $KH_2PO_4$ were added. 200 ul was dispensed into each well of a 96-well microplate, and the plates allowed to cool.

A 1 ppm solution of Avid® was used as a positive control. Deionized water was used as a negative control. Two replicates of test sample or control were used for each assay. 40 ul of supernatant sample prepared as described in Example 1 was dispensed onto the agar surface of microplate wells. A 25 ul aliquot of the pre-adult insect suspension was dispensed into each sample well. The plates were then placed in a fume hood to dry for approximately 2 to 3 hours until the agar solution was dried, but the eggs were not overdried. The microplate was sealed with an airtight substance such as Mylar®, and each well ventilated with a pin press. The plates were incubated at 27° C. for up to 7 days.

After incubation, wells were scored by noting neonate mortality or the degree of larval development. Sample wells containing all dead or stunted larvae were given a score of 1, wells containing some dead and other severely stunted larvae were given a score of 2, live but stunted larvae were scored as 3 and sample wells containing no dead larvae were given a score of 4. Scores were averaged among replicates within each sample. Results are summarized in Table 1.

TABLE 1

| | Score Rating | | | | | |
|---|---|---|---|---|---|---|
| | C. elegans | Corn rootworm | Beet armyworm | Fly | Positive control | Negative control |
| BD #32 | 4.0 | 1.9 | 4.0 | 4.0 | 1.0 | 4.0 |

These results show that the novel *B. thuringiensis* strain produces a secondary metabolite in its supernatant which is effective against corn rootworm, but not against nematodes, armyworm or flies. Thus, BD#32 produces a metabolite which is specifically and uniquely active against corn rootworm.

EXAMPLE 3

Assaying insecticidal activity of a solvent extract of Bacillus strain supernatant To determine the if the insecticidal metabolite in the supernatant would retain activity after extraction, the following experiment was conducted. A 50 mL culture of BD#32 was grown and 50 mL of ethyl acetate added to this culture. The mixture was shaken in separatory funnel for two minutes. The aqueous layer was removed and the organic layer was collected into a bottle containing magnesium sulfate. The organic extract was then filtered into a round bottom flask and the solvent evaporated away.

For the bioassay, the dried organic extract was redissolved in 1 mL of acetone. An aliquot of the redissolved extract was then assayed for insecticidal activity using the procedure described in Example 2. For instance, a 200 uL aliquot of the redissolved extract was removed and diluted to 1 mL with distilled water, to give a 20% acetone or 10× final concentration of the organic extract. The bioassay was performed using pre-adult corn rootworms. Various concentrations of extracted, redissolved supernatant was tested and compared to whole broth and controls. Results are shown in Table 2.

TABLE 2

| Concentration of extract | % mortality |
| --- | --- |
| 10x | 100% |
| 5x | 100% |
| 2.5x | 100% |
| 1x | 25% |
| whole broth | 12.5% |
| 1:1 acetone/water control | 0% |
| water control | 22% |

These results demonstrate that novel strain BD#32 produces a solvent-extractable metabolite which is an effective insecticidal agent.

Having now fully described this invention, it will be appreciated by those skilled in the art that the same can be performed within a wide range of equivalent parameter, concentrations and conditions without departing from the spirit and scope of the invention and without undue experimentation. While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows the scope of the appended claims.

We claim:

1. An isolated, pure culture of a novel strain of *Bacillus thuringiensis* BD#32, NRRL B-21530, or mutants thereof that maintain all the identifying characteristics of the deposited strain, wherein said strain exhibits insecticidal activity against corn rootworm but not against Drosophila.

2. A supernatant obtained from culturing a strain according to claim 1, wherein said supernatant exhibits insecticidal activity against corn rootworm but not against Drosophila.

3. A solvent extract of the supernatant according to claim 2, wherein said extract exhibits insecticidal activity against corn rootworm but not against Drosophila.

4. The solvent extract of claim 3, wherein said solvent is ethyl acetate.

5. A method of treating corn rootworm infection in plants comprising applying an effective amount of a culture according to claim 1 to a plant in need of such treatment.

6. A method of treating corn rootworm infection in plants comprising applying an effective amount of a supernatant according to claim 2 to a plant in need of such treatment.

7. A method of treating corn rootworm infection in plants comprising applying an effective amount of a solvent extract according to claim 3 to a plant in need of such treatment.

* * * * *